United States Patent [19]
Kato

[11] Patent Number: 5,822,446
[45] Date of Patent: Oct. 13, 1998

[54] OPHTHALMOLOGICAL IMAGE PROCESSING SYSTEM FOR RECORDING SPECIFIC PORTIONS OF THE IMAGE

[75] Inventor: Takeyuki Kato, Tokyo, Japan

[73] Assignee: Kabushiki Kaisha TOPCON, Tokyo, Japan

[21] Appl. No.: 810,665

[22] Filed: Mar. 3, 1997

Related U.S. Application Data

[63] Continuation of Ser. No. 512,559, Aug. 8, 1995, abandoned, which is a continuation of Ser. No. 101,045, Aug. 3, 1993, abandoned.

[30] Foreign Application Priority Data

Aug. 4, 1992 [JP] Japan .................................. 4-207980

[51] Int. Cl.⁶ .................................................. G06K 9/00
[52] U.S. Cl. ........................................ 382/128; 382/305
[58] Field of Search .................................. 382/115, 128, 382/173, 282, 199, 283, 131, 132, 175, 180, 181, 190, 201, 209, 224, 305, 306, 307, 309, 312, 319, 281, 117, 264; 351/208, 206; 396/18, 310; 358/453, 464; 378/98.2, 901; 250/587

[56] References Cited

U.S. PATENT DOCUMENTS

| | | | |
|---|---|---|---|
| 4,533,947 | 8/1985 | Smith | 358/111 |
| 4,620,318 | 10/1986 | Hill | 382/2 |
| 4,933,756 | 6/1990 | Sekine | 358/93 |
| 4,977,504 | 12/1990 | Funahashi et al. | 364/413.13 |
| 5,029,220 | 7/1991 | Juday | 382/6 |
| 5,063,606 | 11/1991 | Takamori | 382/283 |
| 5,091,967 | 2/1992 | Ohsawa | 382/283 |
| 5,222,159 | 6/1993 | Kawamura et al. | 382/283 |
| 5,268,967 | 12/1993 | Jang et al. | 382/6 |
| 5,270,924 | 12/1993 | Hideshima | 364/413.13 |
| 5,291,231 | 3/1994 | Hideshima et al. | 351/208 |
| 5,337,164 | 8/1994 | Yabe et al. | 358/487 |

FOREIGN PATENT DOCUMENTS

| | | | |
|---|---|---|---|
| 3-193026 | 8/1991 | Japan | A61B 3/14 |
| 2228847 | 9/1990 | United Kingdom | H04N 1/387 |
| 89/12848 | 12/1989 | WIPO | 382/2 |

OTHER PUBLICATIONS

Tamura et al., "Semiautomatic Leakage Analyzing System for Time Series Flouresein Ocular Fundus Angiography", *Pattern Recognition*, vol. 16, No. 2, 1983, pp. 149–162.

*Primary Examiner*—Leo H. Boudreau
*Assistant Examiner*—Bijan Tadayon
*Attorney, Agent, or Firm*—Finnegan, Henderson, Farabow, Garrett & Dunner, L.L.P.

[57] ABSTRACT

An ophthalmological image processing system includes a data storing and regenerating device for inputting digitized image data concerning an image which includes an ophthalmological image, an arithmetic and control circuit for processing and transmitting image data output by the data storing and regenerating device, an image data processing circuit for processing the image data transmitted by the arithmetic and control circuit, and a monitor TV for outputting an image sent out from the image data processing circuit. The arithmetic and control circuit can transmit only appointed data of the image data.

6 Claims, 11 Drawing Sheets

FIG. 3(b1')

OPHTHALMOLOGICAL IMAGE PROCESSING SYSTEM FOR RECORDING SPECIFIC PORTIONS OF THE IMAGE

This application is a continuation of application Ser. No. 08/512,559 filed Aug. 8, 1995, now abandoned, which is a continuation of Ser. No. 08/101,045 filed Aug. 3, 1993, now abandoned.

BACKGROUND OF THE INVENTION

1. Field of the Invention

This invention relates to an ophthalmological image processing system capable of transmitting a specified part of an ophthalmological image.

2. Description of the Prior Art

Study is being made of an ophthalmological apparatus, such as a fundus camera, in which an ophthalmological image is electronically captured by using a solid-state image sensor, such as an area CCD (Charge Coupled Device), and then image data output by the area CCD are transmitted to a recording unit, such as a still video disk unit, a floppy disk unit, or an optical disk unit, by means of an arithmetic and control unit; and these data are recorded on a data storing medium, such as a still video disk, a floppy disk, or an optical disk.

In order to determine which one of the right and left eyes of a subject was photographed by the fundus camera, the fundus camera includes a mask M disposed in a photographing optical system. As shown in FIG. 11($a$), the mask M has an aperture a and a slotted mark b formed at a specific place on the circumference of the aperture.

An eye fundus image G photographed by using the mask M is circularly formed at the center of the area CCD 60 as shown in FIG. 11($b$). Further, the eye fundus image G is circularly displayed at the center of the display of a monitor TV by means of the arithmetic and control unit, not shown.

The image data output by the area CCD 60 contain both data concerning the circular image G and data concerning a blank space H around the circular image G as shown in Fig. 11($b$). Of those data, only the data concerning the circular image G are required to be transmitted.

However, all the data concerning the image G and the blank space H have heretofore been transmitted in order to display the eye fundus image on the monitor TV or record and regenerate it. A conventional problem in the art is that such transmittance is time-consuming.

As a solution to this problem, it is comprehensible that only the data concerning the circular eye fundus image G be transmitted to record and regenerate the image.

However, in visible fluorescence photography or infrared fluorescence photography, a vascular image of the eye fundus is formed only by fluorescent light emitted from blood vessels of the eye fundus or only fluorescent light emitted from places at which a fluorescent agent injected into the blood vessels is leaking. As a result, parts of the eye fundus from which such fluorescent light is not emitted are dark and invisible. In the method of transmitting only the data concerning the eye fundus image G to record and reproduce or regenerate, since data concerning such dark parts are also transmitted, much time is consumed, and further, a memory capacity for the data concerning the dark parts is needlessly used when recorded.

SUMMARY OF THE INVENTION

It is therefore an object of the invention to provide an ophthalmological image processing system capable of transmitting only the required image data; and thus, shortening the time required for transmission.

To achieve the object, and in accordance with the purpose of the present invention, as embodied and broadly described, the invention is an ophthalmological image processing system including a means for inputting digitized image data concerning an ophthalmological image, means for processing and transmitting the image data sent out from the data inputting means means for processing the image data transmitted from the data transmitting means, and means for outputting an image processed by the image data processing means, the data transmitting means being capable of transmitting only specified data of the image data.

In another aspect, the invention is an ophthalmological image processing system wherein the image data contain data concerning an ophthalmological image and data concerning a blank space around the ophthalmological image; and the data transmitting means is capable of transmitting only the ophthalmological image as specified data.

In a third aspect, the image data inputting means is an ophthalmological instrument in which a mask for giving a fixed shape to an ophthalmological image to be projected, is disposed in front of an area CCD of a photographing optical system; and wherein the image data transmitting means first finds the boundary between a projected ophthalmological image and a blank space around the projected image based on the output of the area CCD; and then transmits data, concerning an ophthalmological image formed within the boundary, to the image data outputting means.

In accordance with a fourth aspect, the image data inputting means is an ophthalmological instrument in which a mask, for giving a fixed shape to an ophthalmological image to be projected, is disposed in front of an area CCD of a photographing optical system and wherein the image data transmitting means first reads address data concerning the boundary between an ophthalmological image to be projected onto the area CCD and a blank space around the image to be projected from a memory means; and then transmits data, concerning an ophthalmological image formed within the boundary to the image outputting means.

In a fifth aspect, the image data transmitting means transmits a part of an ophthalmological image specified by a range specifying means as appointed data to the image outputting means.

In a sixth aspect, the image data transmitting means transmits a part of image data specified by a range specifying means as appointed data to the image outputting means.

In a seventh aspect, one of the image outputting means is a monitor TV and a part of the ophthalmological image displayed on the monitor TV is specified by the range specifying means; and then the specified part is transmitted to the other image outputting means.

In an eighth aspect, an ophthalmological image displayed on the monitor TV is divided into a plurality of selection areas and any of the selection areas is specified by the range specifying means.

In a ninth aspect, the range specifying means can optionally specify a range of the ophthalmological image displayed on the monitor TV.

In a tenth aspect, the range specifying means of the presence invention is a mouse.

In an eleventh aspect, the range specifying means is an arithmetic and control circuit discriminating a papilla and a part around the papilla based on the difference in the amount of light of the data concerning the ophthalmological image.

In a twelfth aspect, the image outputting means is a monitor TV and the image data transferring means transmits only the ophthalmological image to be displayed on the monitor TV.

In a thirteenth aspect, the image outputting means are plurality of terminal units connected with the image data transmitting means via an input and output circuit.

In a fourteenth aspect, the image data transmitting means is connected to an information storing and regenerating unit, and the image data transmitting means transmits and records only the ophthalmological image on the information storing and regenerating unit.

In a fifteenth aspect, the ophthalmological image is transmitted and recorded on the information storing and regenerating unit, and the image data transmitting means causes the ophthalmological image to correspond with identification data and then be recorded.

In a sixteenth aspect, the image outputting means is a monitor TV and the image data transmitting means extracts a part of a plurality of ophthalmological images and causes extracted images to be simultaneously displayed on the monitor TV.

In a seventeenth aspect, an ophthalmological image processing system comprises a means for inputting digitized image data concerning an image which includes a vascular image of an eye fundus formed by fluorescence photography, means for processing and transmitting the image data sent out from the image data inputting means, means for processing the image data transmitted from the data transmitting means, and means for outputting an image processed by the image data processing means, and the data transmitting means is capable of transmitting only data concerning a part having more than a given amount of light of the eye fundus vascular image formed by fluorescence photography.

According to an eighteenth aspect, the data concerning the part having more than a given amount of light, consist of data concerning an amount of light and address data corresponding to the respective data concerning an amount of light.

According to a nineteenth aspect, the data transmitting means of the seventeenth aspect transmits only data concerning a part having more than a given amount of light of the eye fundus vascular image formed by fluorescence photography.

According to a twenty-first aspect, the given amount of light of the seventeenth aspect is between a first level and a second level.

According to a twenty-first aspect, the ophthalmological image of the first aspect is specified by matrices arrayed in rows and columns.

According to a twenty-second aspect, the appointed data of the first aspect includes code data together with the image data.

These and other objects, features and advantages of the present invention will be well appreciated upon reading of the following description of the invention when taken in conjunction with the attached drawings with the understanding that some modifications, variations and changes of the same could be made by a skilled person in the art to which the invention pertains without departing from the sprit of the invention or the scope of claims appended hereto.

DESCRIPTION OF THE PREFERRED EMBODIMENTS

Figure 1:
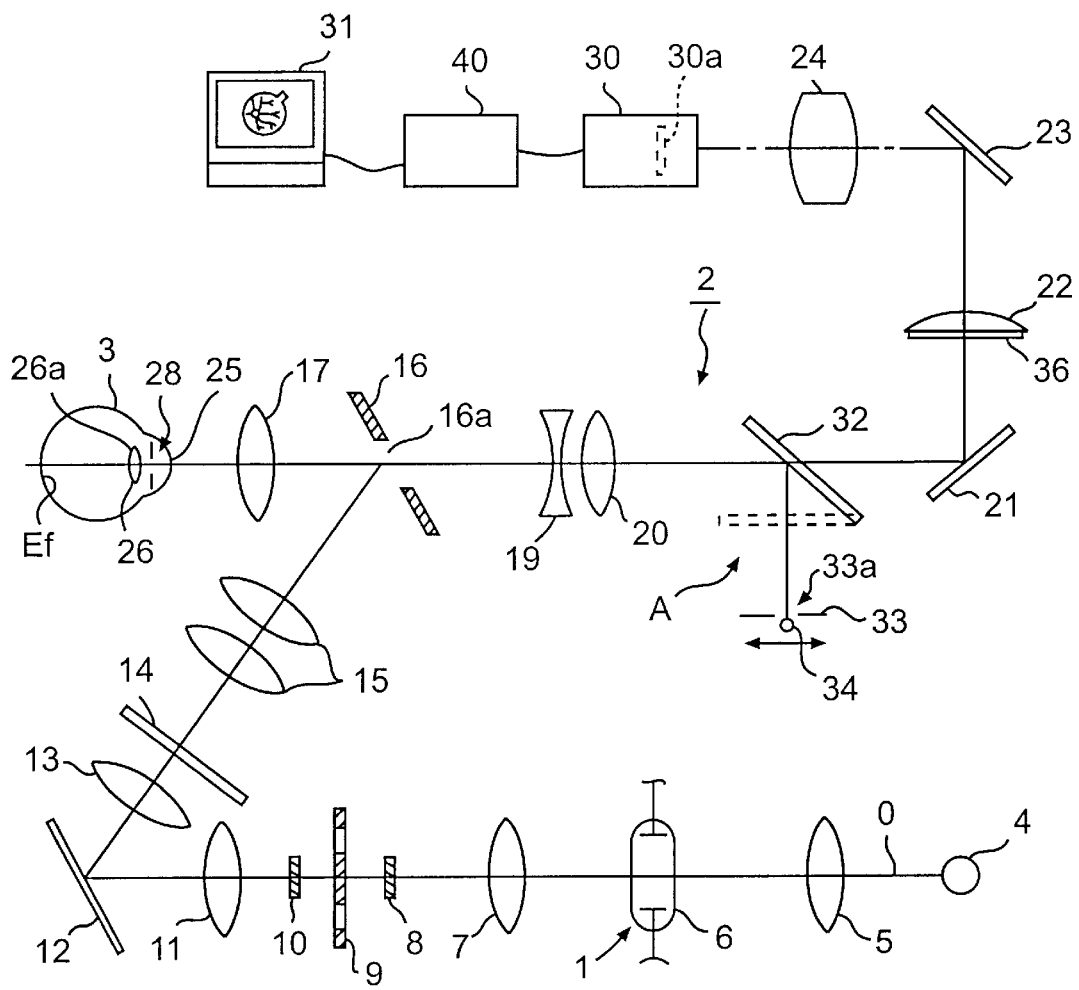
FIG. 1 is a schematic drawing of an optical system of a fundus camera for use in an ophthalmological image processing system according to the invention.

FIG. 1 shows a first embodiment of an optical system of a fundus camera (photographing device). Referring to FIG. 1, the reference numeral 1 designates an illuminating optical system of the fundus camera, the reference numeral 2 designates an observing and photographing optical system, and the reference numeral 3 designates an eye of a subject.

The illuminating optical system 1 includes an illuminating optical system for observation and an illuminating optical system for photography.

The illuminating optical system for photography includes a xenon lamp 6, a condenser lens 7, a small type light shading plate 8, a ring diaphragm 9, a small type light shading plate 10, a relay lens 15, a reflecting mirror 12, a relay lens 13, a black spot plate 14, a relay lens 15, a perforated mirror 16, and an objective lens 17 in this order. Illuminating light for photography emitted from the xenon lamp 6 is projected onto a fundus Ef of a subject's eye 3 through the respective optical members of the condenser lens 7 to the objective lens 17. An exciter filter E1 for visible fluorescence and an exciter filter E2 for infrared fluorescence are retractably disposed between the xenon lamp 6 and the condenser lens 7.

The illuminating optical system for observation includes a halogen lamp 4 as a source for observation, a condenser lens 5, and optical members of the condenser lens 7 to the objective lens 17 each mentioned above. Illuminating light for observation emitted from the halogen lamp 4 is projected onto the fundus Ef through the respective optical members of the condenser lens 5 to the objective lens 17.

The light shading plate 8 is conjugate with a cornea 25 of the eye 3, the ring diaphragm 9 is conjugate with a pupil 28 of the eye 3, and the light shading plate 10 is conjugate with the back surface 26a of a lens 26 of the eye 3. The black spot plate 14 serves as a light shading plate for prohibiting light reflected by the surface of the objective lens 17 from passing through a hole 16a of the perforated mirror 16.

The observing and photographing optical system 2 includes an objective lens 17 disposed before the eye 3, a focusing lens 19, an image forming lens 20, a mirror 21, a field lens 22 conjugate with the eye fundus Ef, a reflecting mirror 23, and a relax lens 24. A barrier filter for visible fluorescence (not shown) and a barrier filter B2 for infrared fluorescence are retractably disposed between the perforated mirror 16 and the focusing lens 19.

Reflection light from the eye fundus Ef reaches an area CCD 30a (image data inputting means, image sensing means) of a TV camera 30 via the objective lens 17, the focusing lens 19, the image forming lens 20, the mirror 21, the field lens 22, the reflecting mirror 23, the relay lens 24, and a mask 36, and forms an eye fundus image on the area CCD 30a. The mask 36 has an aperture 36a and a slotted mark 36b formed on the circumference of the aperture as shown in FIG. 4.

An image signal sent out from the area CCD 30a is input to a monitor TV 31 (image displaying means) generally via an arithmetic and control circuit 41 (FIG. 4) of a camera control circuit 40, which will be described hereinafter, a contact of a circuit changing switch 41a, and a D/A converter 41b in order to display the eye fundus image on the monitor TV 31 in real time (see FIG. 2). A type of monitor TV including a self-contained circuit equivalent to the D/A converter 41b may be used instead of the monitor TV 31.

An eye fixing optical system A includes a half mirror 32 disposed retractably between the image forming lens 20 and the mirror 21, a mask 33 having a small hole 33a as a target upon which the eyes of the subject are fixed, the mask 33 being disposed conjugate with the eye fundus Ef, and a light source, such as a light emitting diode, disposed just behind the hole 33a. The mask 33 and the source 34 for fixing the eyes are included in a target driving apparatus 35, such as an X–Y table, not shown, electrically controlled and driven by, e. g., a pulse motor. Which of the right and left eyes was photographed is detected by a right and left eyes discriminating means 35' and then the target driving apparatus 35 is moved so as to locate a papilla (optic disk) 71 and a yellow spot 72 each approximately equally distant from the center of a display 31A as shown in FIG. 2.

Figure 4:
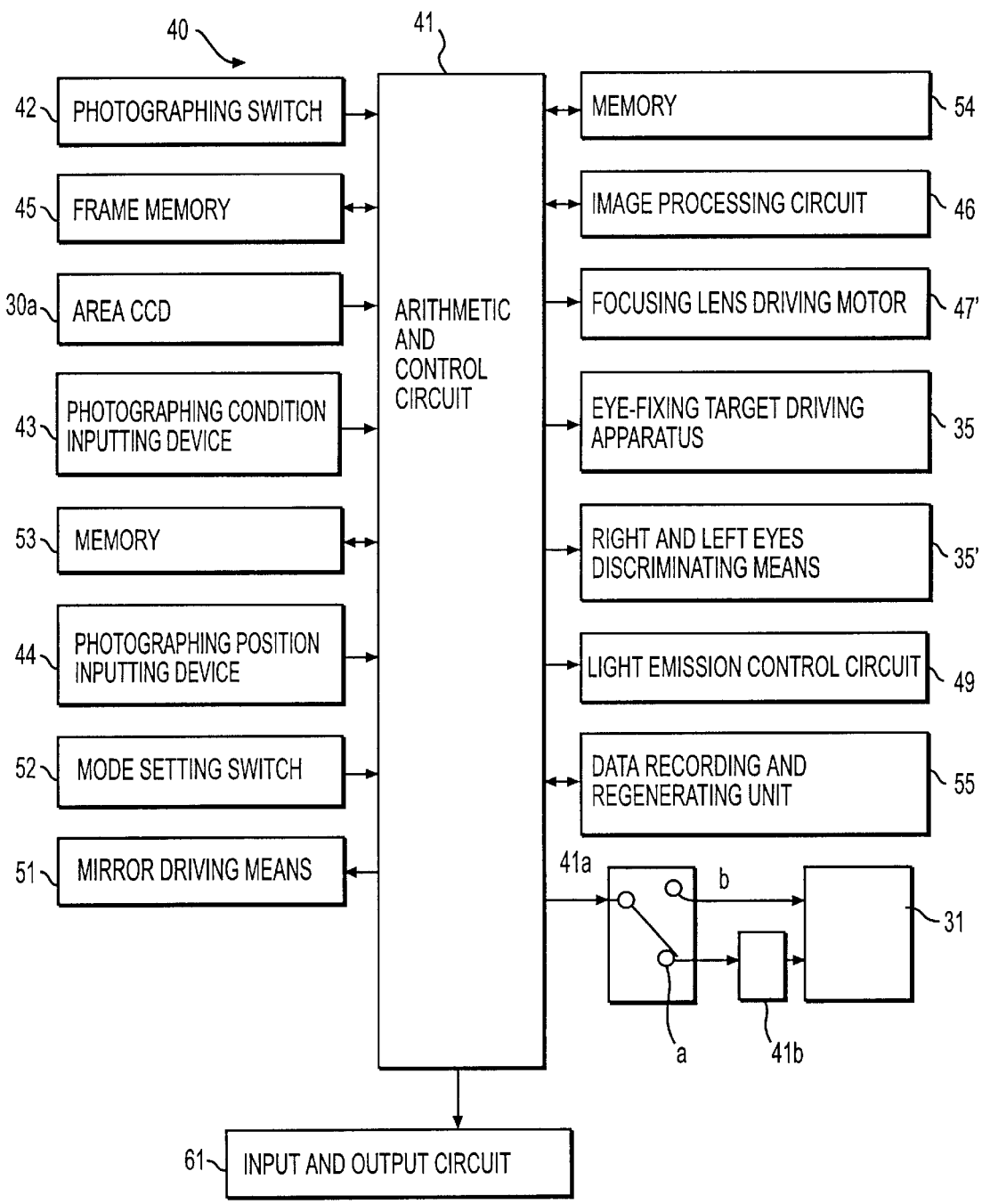
FIG. 4 is a block diagram of a control circuit of the fundus camera of FIG. 1.

As shown in FIG. 4, the camera control circuit 40 includes the arithmetic and control circuit 41 serving as image data transmitting means. To the arithmetic and control circuit 41 are input an on-signal from a photographing switch 42, a photographing condition informing signal from a photographing condition inputting device such as a keyboard, and a photographing position signal from a photographing position inputting device such as a mouse, keyboard, or light pen. The photographing switch 42 is designed to be turned on to output a control signal by the first slight push and output a photography starting signal by the second full push.

The arithmetic and control circuit 41 is connected with a frame memory 45, an image processing circuit 46 as an image processing means, a focusing lens driving motor 47', the discriminating means 35' for detecting which of the right and left eyes was photographed based on a position in the right and left directions of the camera including the above mentioned optical system, and a light emission control circuit 49.

Further, the arithmetic and control circuit 41 is connected with a mirror driving means 51 such as a solenoid for inserting a half mirror 32 in the photographing optical system or removing it from the same, a mode setting switch 52 in an observing and photographing mode, a memory 53 such as a RAM, a memory 54 such as a RAM, a data recording and regenerating unit 55 (image inputting means) such as an optical disk unit or floppy disk unit, the area CCD 30a, and the monitor TV 31.

The arithmetic and control circuit 41 causes an eye fundus image (medical electronic image) photographed by the area CCD 30a as an image sensing means to be recorded on a data storing medium such as an optical disk or floppy disk via the data recording and regenerating unit 55 and further to be displayed on the display 31A of the monitor TV 31 (electronic image displaying device).

A description will now be given of a data transmitting function of the arithmetic and control circuit 41 in photographing, recording, and regenerating the ophthalmological image.

<New Photography, Record, and Regeneration>

When a power, not shown, of the ophthalmological apparatus is turned on, the arithmetic and control circuit 41 causes the halogen lamp 4 to be lighted. While the lamp 4 is lighted, aligning and focusing are made with respect to the eye fundus Ef. When those are completed, illumination light emitted from the halogen lamp 4 is projected onto the eye fundus via the illuminating optical system 1 and then it is reflected therefrom.

The right and left eyes discriminating means 35' outputs a signal for identifying that the eye fundus under observation belongs to the right or left eye. The arithmetic and control circuit 41 causes the identification signal (discrimination signal) to be stored as identification data (discrimination data) in the memory 53.

On the other hand, the reflection light from the eye fundus Ef is guided to the area CCD (image sensing means) of the TV camera 30 via the respective optical members of the objective lens 17 to the image forming lens 20 of the observing and photographing optical system 2, the mirror 21, the mask 36 conjugate with the eye fundus Ef, the field lens 22, the reflecting mirror 23, the relay lens 24.

Figure 5A:
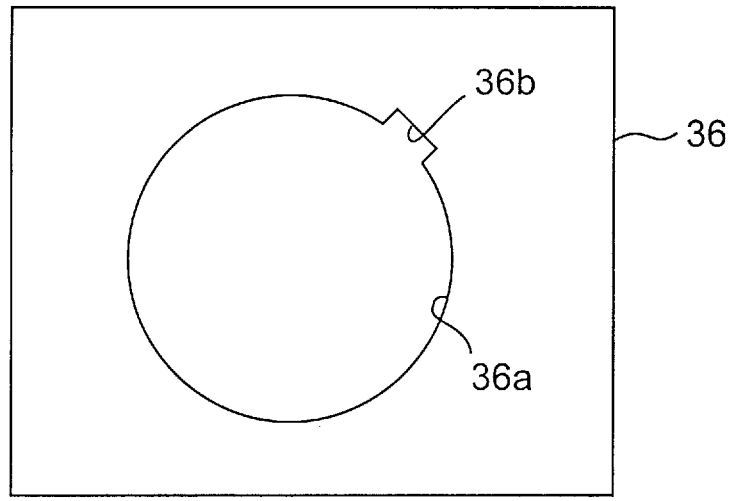
FIGS. 5(a) and 5(b) are views showing a mask of FIG. 1 and an eye fundus image formed on an area CCD of FIG. 1, respectively.
Figure 5B:
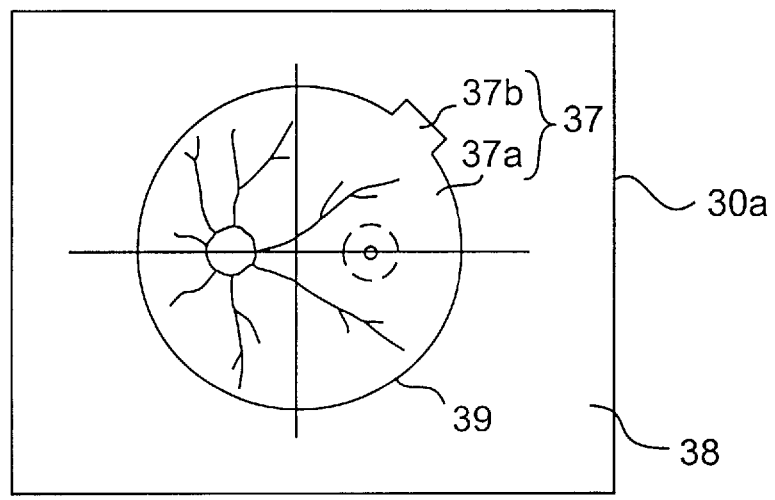

Thereby, an image 37 of the eye fundus Ef is formed on the area CCD 30a as shown in FIG. 5. This eye fundus image 37 has a circular part 37a corresponding to the aperture 36a of the mask 36 shown in FIG. 5(a) and a part 37b corresponding to the slotted mark 36b. Further, around the eye fundus image 37 on the area CCD 30a, a blank space 38 results from the mask 36.

When the discrimination signal is input by the right and left eyes discriminating means 35', the arithmetic and control circuit 41 reads image data concerning both the eye fundus image 37 and the blank space 38 for a first frame by scanning the whole of the area CCD 30a and then causes the image data to be stored in the frame memory 45.

At this time, the arithmetic and control circuit 41 calculates the difference in amount of light between the eye fundus image 37 and the blank space 38 based on data concerning the address and amount of light of each picture element of the area CCD 30a or data stored in the frame memory 45 to obtain address data concerning boundary 39 between the eye fundus image 37 and the blank space 38 and then causes the address data to correspond to the identification data concerning the right or left eye in order to restore the address data in the memory 53. By finding the boundary 39 in such a way, the ophthalmological image to be transmitted, or the part to which data concerning the eye fundus image to be transmitted belong, is decided to be within the boundary 39.

The operation for finding the boundary 39 is carried out only once when the ophthalmological image is first observed and resulting data concerning the boundary 39 are used whenever transmitted. These data concerning the boundary 39 may be beforehand recorded on a storing medium, such as an optical disk, floppy disk, or still video disk, via the data recording and regenerating unit 55 and be extracted from the medium on occasion.

Next, the arithmetic and control circuit 41 transmits only the data concerning the eye fundus image 37 inside the blank space 38 from the frame memory 45 to the image processing circuit 46 and then displays the eye fundus image 37 on the monitor TV 31 via the image processing circuit 46.

After that, the arithmetic and control circuit 41 reads the image data of the area CCD 30a and then transmits them to the frame memory 45 in order to store the image data for one frame in the frame memory 45. The arithmetic and control circuit 41 transmits only the data concerning the eye fundus image within the boundary 39 stored in the frame memory 45 from the frame memory 45 to the image processing circuit 46 and then causes the eye fundus image 37 to be displayed on the monitor TV 31 via the image processing circuit 46 as shown in FIG. 2.

If the address data concerning the boundary 39 are known, they are previously stored in a ROM or the like. Accordingly, the image data to be read for the first frame are only the data concerning the eye fundus image. In this case, since the position of the slotted mark of the mask 36 depends on the right or left eye to be observed, the data concerning the boundary 39 are previously stored in the ROM so as to respond to an identification signal output by the right and left eyes discriminating means 35'.

When the eye fundus image is observed in such a way, the circuit changing switch 41a keeps contacting with the contact a. A digital signal output by the area CCD 30a is input to the D/A converter 41b to be converted into an analogue signal via the arithmetic and control circuit 41 and the circuit changing switch 41a. The resulting analogue signal is input to the monitor TV 31 to display the eye fundus image in real time.

After the eye fundus image is observed in such a way, the circuit changing switch 41a is first turned to contact with a contact b to photograph the eye fundus. Some filters, not shown, are then disposed in the respective optical systems and the xenon lamp 6 is lighted. Light for photography emitted from the xenon lamp 6 is projected onto the eye fundus Ef via the illuminating optical system 1. And then light reflected from the eye fundus Ef is guided to the area CCD 30a via the observing and photographing optical system 2, so that the eye fundus is photographed.

A digital image signal output by the area CCD 30a is input to the monitor TV 31 via the arithmetic and control circuit 41 and the circuit changing switch 41a to display a digital image of the eye fundus on the monitor TV 31. At this time, only the eye fundus image within the boundary 39 is transmitted as mentioned above.

Figure 2A:
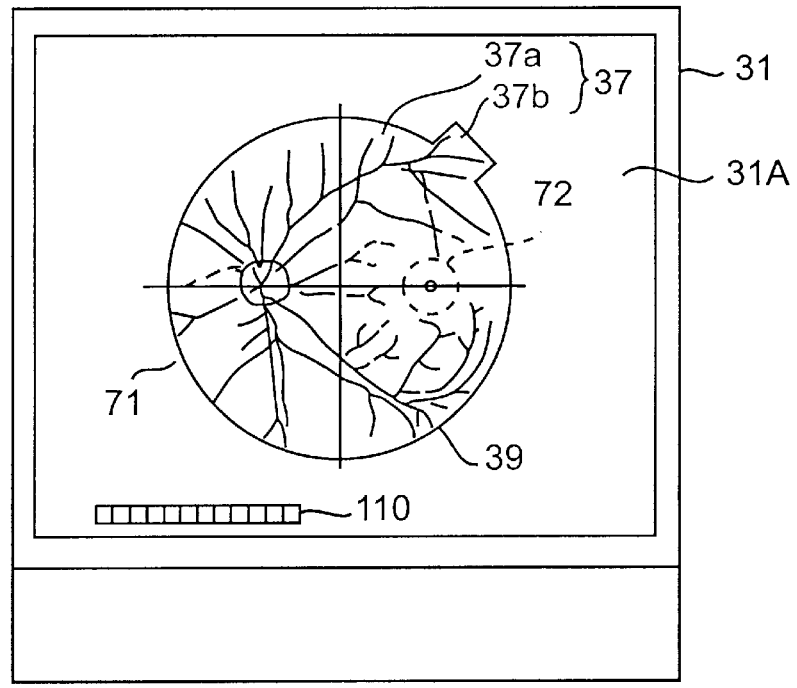
FIGS. 2(a) and 2(b) are enlarged views of a monitor TV of FIG. 1.

As shown in FIG. 2, together with the eye fundus image, an image of code data 110 concerning photographing conditions and so on is also displayed on the blank space 38 which was produced by the mask. The image of the code data 110 may also be transmitted under the same process as that of the eye fundus image within the boundary 39.

When the eye fundus Ef is photographed by visible fluorescence, fluorescein for visible fluorescence is first injected into a subject. After the eye fundus Ef is observed as mentioned above, the circuit changing switch 41a is turned to contact with the contact b, and then the exciter filter E1 for visible fluorescence is inserted into the optical path between the xenon lamp 6 and the condenser lens 7; and further, the barrier filter B1 for visible fluorescence is inserted into the optical path between the perforated mirror 16 and the focusing lens 19.

Next, the xenon lamp 6 is lighted. Visible excitation light having a wavelength capable of exciting the fluorescein is then guided from the xenon lamp 6 to the eye fundus Ef via the illuminating optical system 1 and the exciter filter E1 to illuminate the eye fundus Ef.

The visible excitation light is absorbed by the fluorescein inside the blood vessels of the eye fundus Ef, and then excites the fluorescein. Thereby, visible fluorescent light is emitted from the fluorescein. The visible fluorescent light is guided to the area CCD 30a via the observing and photographing optical system 2. Accordingly, an image of the blood vessels of the eye fundus Ef is formed by the visible fluorescent light on the area CCD 30a as shown in FIGS. 3(a) to 3(c) to perform the visible fluorescence photography thereof.

Figure 3A:
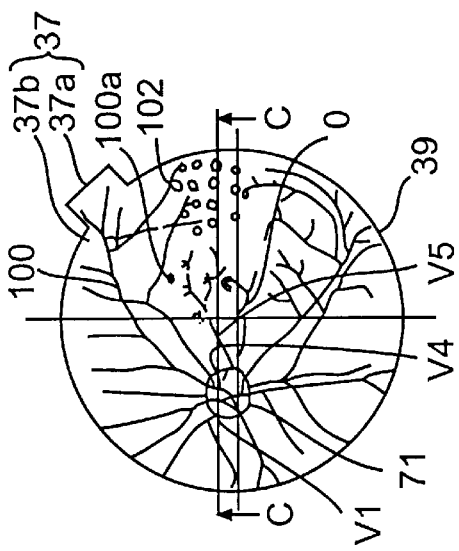
FIGS. 3(a), 3(b), 3(c), 3(a1), 3(b1), 3(c1), 3(b1'), 3(b2), and 3(c2) are schematic views showing a change with the lapse of time in the blood vessels of an eye fundus when photographed by fluorescence, where (a1), (b1), and (c1) are descriptive drawings of fluorescence brightness of the blood vessels, (b2) is a descriptive drawing of fluorescence brightness of a discharge portion of blood from the blood vessels, (c2) is a descriptive drawing of fluorescence brightness of a bullous portion generated around a laser coagulation after a retina is coagulated by a laser, and (b1') is a descriptive drawing showing that the number of slice levels corresponding to fluorescence brightness is increased.

FIG. 3(a) shows a vascular image of the eye fundus in a relatively early stage of fluorescence photography and 3(c) shows the image in the latest of the three. Referring to 3(a), a papilla (optic disk) 71 surrounded by the line 71' is photographically darker than its surroundings. Referring to 3(b), since fluorescent light is emitted by a fluorescent agent flowing from capillaries to the papilla, the papilla is relatively brighter than the surroundings. Referring to 3(c), a quantity of the fluorescent agent flowing to the papilla is larger than that in the blood vessels 100 of the eye fundus, and therefore an amount of the fluorescent light emitted from the papilla is larger than that in the blood vessels 100.

Figure 3B:
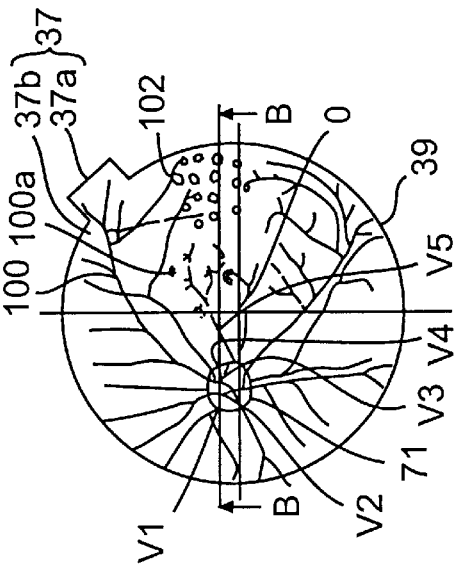
Figure 3C:
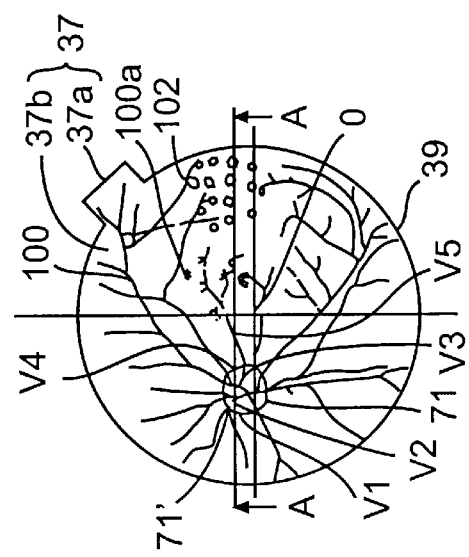
Figure 3:
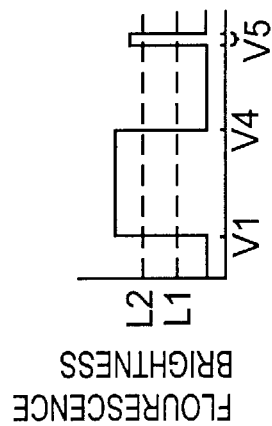
Figure 3:
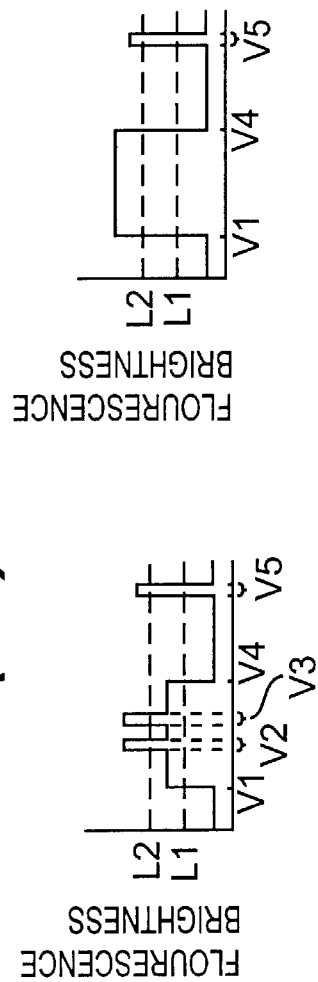
Figure 3:
Figure 3:
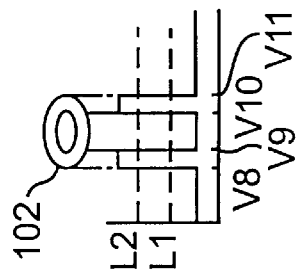
Figure 3:
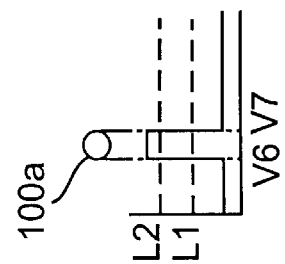
Figure 3:
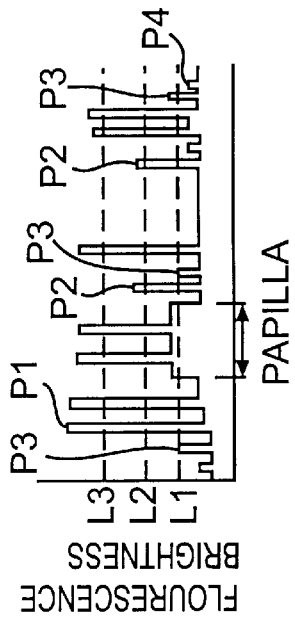

FIG. 3(a1) shows an amount of fluorescent light emitted from the neighborhood of the papilla along the line A—A of 3(a), FIG. 3(b1) shows an amount of fluorescent light emitted from the neighborhood of the papilla along the line B—B of FIG. 3(b), 3(c1) shows an amount of fluorescent light emitted from the neighborhood of the papilla along the line C—C of 3(c), 3(b2) shows an amount of fluorescent light emitted from a discharge portion 100a of blood from blood vessels of the eye fundus of 3(b), and 3(c2) shows an amount of fluorescent light emitted from blisters generated around laser coagulations of 3(c). The reference numerals VI to VII designating points in 3(a) to 3(c) respond to those in FIG. 3(a1) to FIG. 3(c2), respectively.

Figure 2B:
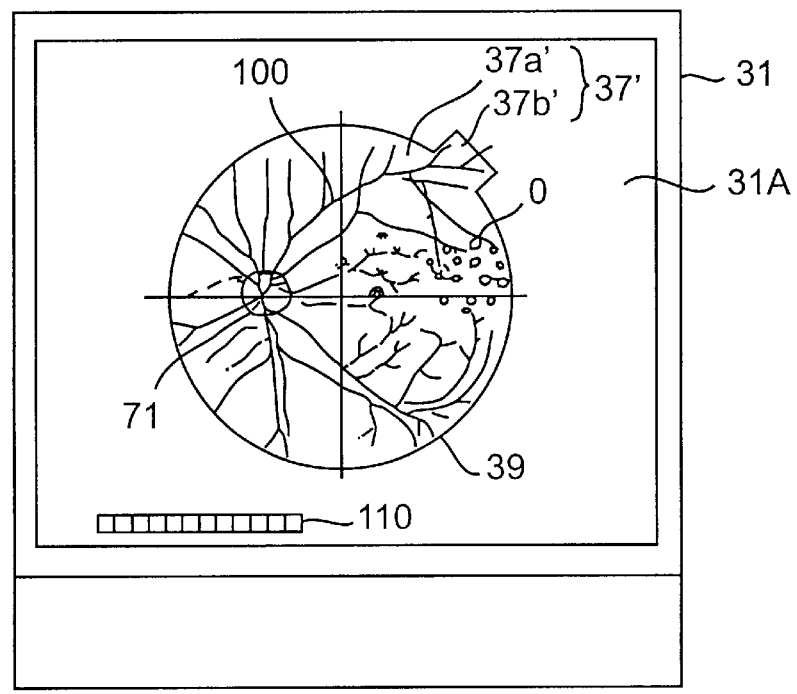

When the blood vessels of the eye fundus are photographed by the visible fluorescent light, a digital image signal output by the area CCD 30a is input to the monitor TV 31 via the control circuit 41 and the circuit changing switch 41a, so that a visible fluorescence image 37' is displayed on the monitor TV 31 as shown in FIG. 2(b). The reference numeral 100 in FIG. 2(b) designates an eye fundus vascular image as a visible fluorescence image.

At this time, only the eye fundus vascular image within the boundary 39 is transmitted from the area CCD 30a the same as mentioned above. Since the address of the boundary 39 is known, only the range within the boundary 39 is scanned, and then address data and respective amounts of light of picture elements having more than a given level L1 of the picture elements of the area CCD 30a, are transmitted to the arithmetic and control circuit 41. The arithmetic and control circuit 41 causes the frame memory 45 to form the eye fundus vascular image 100 of the fluorescent light based on the transmitted data, and then causes the image 100 to be displayed on the monitor TV 31.

To transmit those data to the arithmetic and control circuit 41, a method may be adopted in which the value of the address data concerning the picture elements having an amount of light more than a given level L1 of the picture elements of the area CCD 30a is set by 1 and the value of those less than the level L1 is set by 0 to process the eye fundus vascular image as an image having only signals of 0 and 1. In FIG. 3(a) through 3(c) and (a1)–(c2) though the slice level is set at L1 including fluorescent light emitted from the papilla 71, it may be set at L2 or L3 not including the fluorescent light. Further, a part of the image to be processed may be determined between L1 and L2 or L2 and L3 (L1<L2<L3).

Likewise, when the eye fundus Ef is photographed by infrared fluorescence, ICG (indocyanine green) for infrared fluorescence is first injected into the subject. After the eye fundus Ef is observed as mentioned above, the circuit changing switch 41a is turned to contact with the contact b and then, the exciter filter E2 for infrared fluorescence is inserted into the optical path between the xenon lamp 6 and the condenser lens 7, and further the barrier filter B2 for infrared fluorescence is inserted into the optical path between the perforated mirror 16 and the focusing lens 19.

Next, the xenon lamp 6 is lighted. Infrared excitation light having a wavelength capable of exciting the ICG is then guided from the xenon lamp 6 to the eye fundus Ef via the illuminating optical system 1 and the exciter filter E2 to illuminate the eye fundus Ef.

The infrared excitation light is absorbed by the ICG inside the blood vessels of the eye fundus Ef and then excites the ICG. Thereby, infrared fluorescent light is emitted from the ICG. The infrared fluorescent light is guided to the area CCD 30a via the observing and photographing optical system 2. Accordingly, an image of the blood vessels of the eye fundus Ef is formed by the infrared fluorescent light on the area CCD 30a to perform the infrared fluorescence photography thereof.

When the blood vessels of the eye fundus is photographed by the fluorescent light, a digital image signal output by the area CCD 30a is input to the monitor TV 31 via the control circuit 41 and the circuit changing switch 41a, so that an infrared fluorescence image is displayed on the monitor TV 31.

At this time, only the eye fundus vascular image within the boundary 39 is transmitted from the area CCD 30a the same as mentioned above. Since the address of the boundary 39 is known, only the range within the boundary 39 is scanned; and then address data and respective amounts of light of picture elements having more than a given level L1 (as a predetermined slice level) of the picture elements of the area CCD 30a are transmitted to the arithmetic and control circuit 41. The arithmetic and control circuit 41 causes the frame memory 45 to form the eye fundus vascular image of the fluorescent light based on the transmitted data and then causes the vascular image to be displayed on the monitor TV 31.

To transmit those data to the arithmetic and control circuit 41, a method may be adopted in which the value of the address data concerning the picture elements having an amount of light more than a given level L1 of the picture elements of the area CCD 30a is set by 1 and the value of those less than the level L1 is set by 0 to process the eye fundus vascular image as an image having only signals of 0 and 1.

An ophthalmological image formed by such fluorescence photography as mentioned above, that is, an eye fundus blood vessel image, blood discharging portion image, or blister image is different in width or shape from the other. In other words, the eye fundus blood vessel image is long and slender, the blood discharging portion image is a spot with a fixed width or diameter, and the blister image of a blister generated around a laser coagulation on the retina of the eye fundus is a ring with an approximately fixed diameter. Therefore, if the ophthalmological image is processed as an image having signals 0 and 1 as mentioned above, the arithmetic and control circuit 41 can automatically detect and record a diseased part of a discharge of blood or a laser coagulation portion on the retina.

In practice, since an amount of the fluorescent light emitted from the blood vessels of the eye fundus depends on the thickness of each blood vessel, its fluorescence brightness can be shown, for example, as in FIG. 3(b1'). P1 is the fluorescence brightness (amount of fluorescent light) of a relatively thick blood vessel of the eye fundus, P2 is the fluorescence brightness of a medium-thick blood vessel thereof, and P3 is the fluorescence brightness of a capillary vessel thereof. If slice levels are set at L1, L2, and L3, an image of only the relatively thick blood vessels, an image of only the medium-thick blood vessels, or an image of the capillary vessels can be selected to display it on the monitor TV by judging that the blood vessels having the brightness P1, P2, or P3 respond to which of the level slices L1 to L3. Accordingly, a diagnosis of a diseased part of the eye fundus can be easily made. Since a discharge portion of blood from blood vessels becomes greater in fluorescence brightness than blood vessels especially in the latter stage of fluorescence, it can be also applied to a diagnosis of the existence of a discharge of blood. Such selection and judgment on the images are carried out by the arithmetic and control circuit 41.

As for data concerning an eye fundus image formed by the visible color photography, only the data concerning the eye fundus image 37 within the boundary 39 are recorded on a storing medium, such as an optical disk, floppy disk, or still video disk, via the data recording and regenerating unit 55.

On the other hand, as for data concerning an eye fundus vascular image formed by the fluorescence photography, only the data concerning addresses and amounts of light of picture elements having more than a given level of all the picture elements of the area CCD 30a are recorded on the storing medium via the data recording and regenerating unit 55.

Therefore, when the ophthalmological image is regenerated by the data recording and regenerating unit 55, the same data concerning the eye fundus image 37 within the boundary 39 or the same data concerning the vascular image are read from the storing medium.

<Regeneration Of Old Image Data Having, Data Concerning Both A Blank Space And An Ophthalmological Image>

There are image data concerning a blank space around an eye fundus image and an ophthalmological image. Many cases are also thinkable where such old image data and information about photographing conditions corresponding to the old image data are recorded on a data storing medium such as a floppy disk. The photographing conditions are, for example, an ID number of a subject, name, age, sex, distinction between right and left eyes, amount of light for photography, and sort of a filter to be used.

In such plenty of old image data recorded on the data storing medium, shapes and sizes of light shading masks used for forming many ophthalmological images of the right or left eye can be considered to be all the same, because all the images are certainly formed with a single eye fundus camera.

Therefore, to regenerate the old image data, the arithmetic and control circuit 41 is first caused to find the boundary line between an eye fundus image and a blank space produced by a mask used for obtaining the data. This process is applied to only one image, which was formed for the first time, of all the images of the right or left eye.

To find the boundary, the arithmetic and control circuit 41 first actuates the data recording and regenerating unit 55, and then causes the unit 55 to read and input the old image data to the frame memory 45.

In the same way as mentioned above, the arithmetic and control circuit 41 calculates and obtains address data concerning the boundary 39 base on the difference in amount of light between the eye fundus image and the blank space and further clarifies the distinction between the right and left eyes based on the position of a part corresponding to the slotted mark 36b, and causes the memory 53 to record the address data together with the distinction data.

By finding the boundary 39 in this way, the ophthalmological image to be transmitted or the range relating to data concerning the eye fundus to be transmitted belong is decided to be within the boundary 39. The operation for finding the boundary 39 is carried out only once when the old image data are first input to the frame memory 45 each for the right and left eyes.

The arithmetic and control circuit 41 transmits only the data concerning the eye fundus image inside the blank space 36 from the frame memory 45 to the image processing circuit 45 and then causes the eye fundus image to be displayed on the monitor TV via the image processing circuit 45.

Based on the address data concerning the boundary 39 found in such a way as mentioned above, only the data within the boundary 39 are transmitted to the monitor TV 31.
<Regeneration And Transmittance Of Image Data Obtained By Fluorescence Photography>

A situation is also feasible where the old image data mentioned above include data concerning an eye fundus vascular image photographed by visible fluorescence or infrared fluorescence. Whether or not it is data obtained by fluorescence photography is determined by the sort of a filter contained in information about photographing conditions.

Therefore, when the arithmetic and control circuit 41 actuates the data recording and regenerating unit 55 and then causes the unit 55, to read and input the old image data to the frame memory 45, the arithmetic and control circuit 41 is caused to judge whether or not it is data obtained by fluorescence photography.

If the arithmetic and control circuit 41 judges that it is by fluorescence photography, the arithmetic and control circuit 41 calculates and obtains address data concerning the boundary 39 based on the difference in the amount of light between the eye fundus image and the blank space; and further clarifies the distinction between the right and left eyes based on the position of a part corresponding to the slotted mark 36b, and causes the memory 53 to record the address data together with the distinction data in the same way as mentioned above. The operation for finding the boundary 39 is also carried out only once when the old image data are first input to the frame memory 45 for each of the right and left eyes.

Further, the arithmetic and control circuit 41 finds address data, whose amount of fluorescent light is more than a given level in the image within the boundary 39, and its amount of fluorescent light. In other words, the circuit 41 finds address data and its amount of fluorescent light concerning a part of the blood vessels of the eye fundus from which fluorescent light is emitted or concerning a place of a fluorescent agent leaked from the blood vessels.

The data concerning the boundary 39 or the address data and its amount of fluorescent light concerning an eye fundus vascular image or the like formed by fluorescence photography are recorded on a new medium via the data recording and regenerating unit 55 and retrieved as occasion demands.

In the first embodiment, all the data concerning the eye fundus image 37 within the boundary 39 were transmitted. However, the invention is not necessarily limited to the above. For example, a part of the eye fundus image (e.g., a diseased part of the eye fundus) may be appointed to be transmitted in order to record and regenerate it. To appoint it, a method may be adopted in which the eye fundus image is divided into four parts consisting of, e.g., a top right-hand part, down right-hand part, top left-hand part, and down left-hand part and a selection menu of the four parts is displayed on the monitor TV 31 to select any part with a cursor key of a keyboard or a mouse, or in which an optional range of the eye fundus image is appointed with the mouse.

Figure 6:
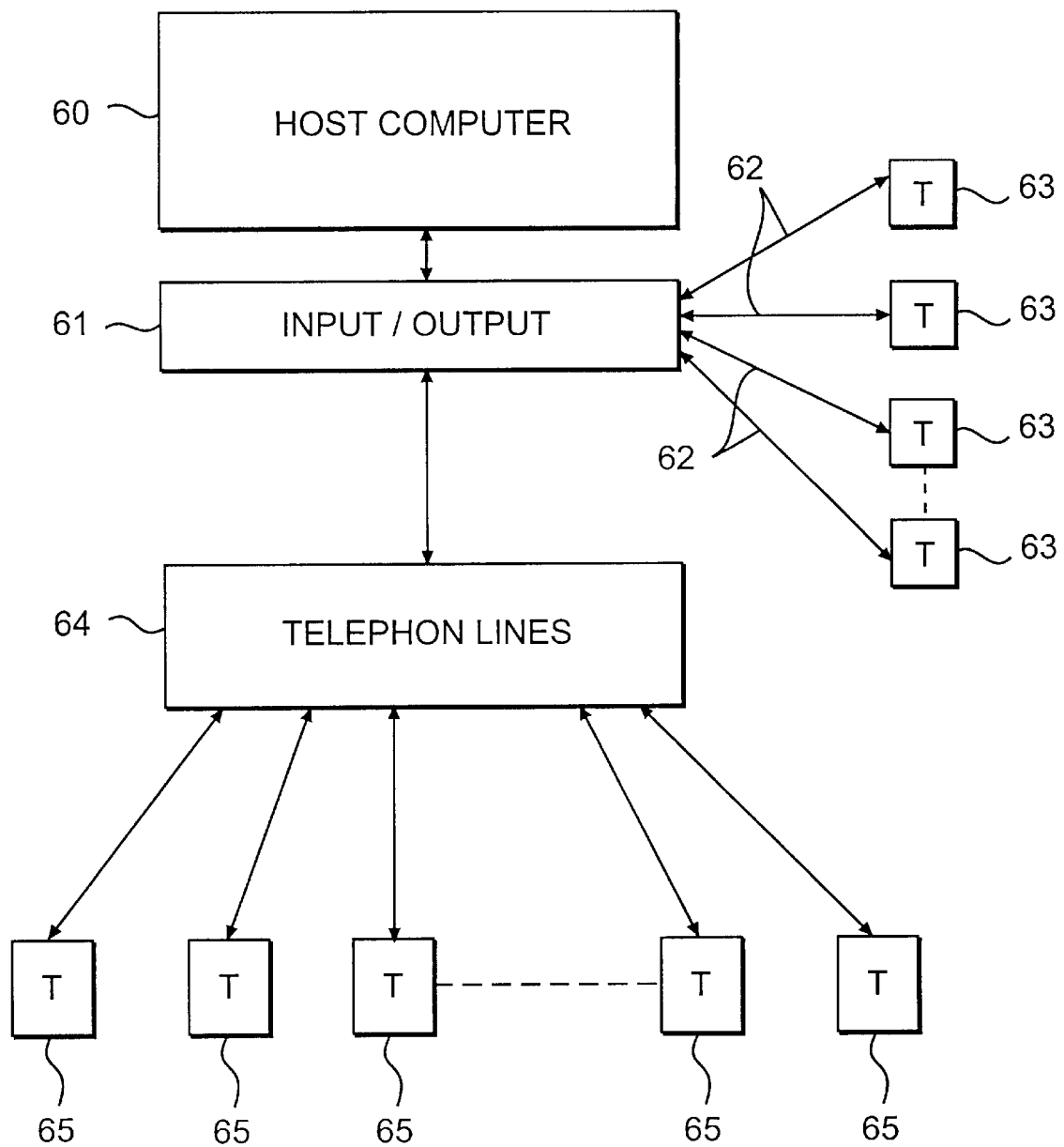
FIG. 6 is a schematic block diagram of a practical application of the ophthalmological image processing system shown in FIGS. 1 to 5.

Such a system as shown in FIG. 6 may be installed. Referring to the second embodiment of FIG. 6, a host computer system 60 including the control circuit 40 is connected with a plurality of terminal equipments 63 via an input and output circuit 61 and cables 62; or the host computer system 60 is connected with a plurality of terminal equipments 65 via telephone lines 64 so that the eye fundus image stored in the host computer system 60 in such a way as mentioned above, is retrieved or operated by the terminal equipments 63 or 65 or, to the contrary, the fundus image transmitted from the terminal equipments 63 or 65 is stored in the host computer system 60. Each of the terminal equipments 63, 65 includes a monitor TV, keyboard, mouse and so forth.

As an example of the practical use of the ophthalmological image processing system according to the invention, the host computer system 60 is placed in a computer room of a general hospital, the terminal equipments 63 are placed in consulting rooms or private rooms of doctors in the general hospital, and the terminal equipments 65 are placed in local hospitals.

FIGS. 7 to 10 show a third embodiment of the invention.

Figure 7A:
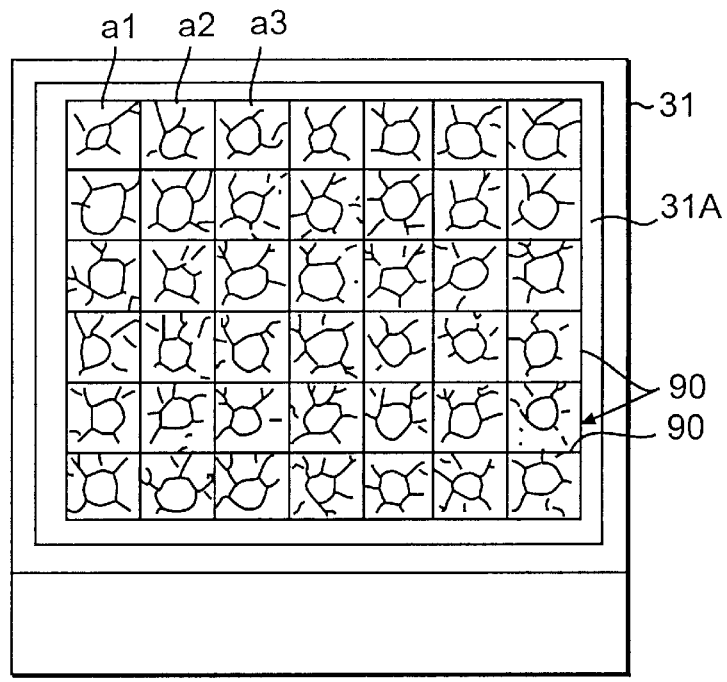
FIGS. 7(a) and 7(b) show a third embodiment of ophthalmological images displayed on a monitor TV by the ophthalmological image processing system according to the invention.
Figure 7B:
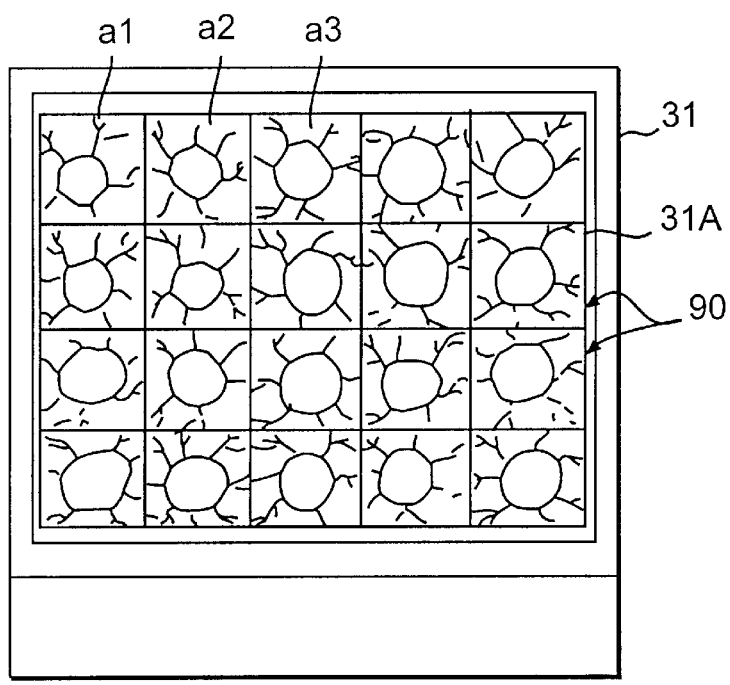

In this embodiment, a specified part only, such as a papilla or yellow spot, is extracted from respective image data, many images of the specified part are simultaneously displayed as shown FIG. 7(a) and 7(b), and desired images of the many images are again displayed thereon or transmitted.

At the same time, a mode selection menu representing, for example, (1.retrieval 2.display 3.transmittance) is displayed on the monitor TV 31.
<Extraction By A Mouse Or Cursor Key>

When the mode "retrieval" is selected by a mouse or keyboard, the arithmetic and control circuit 41 causes the data recording and regenerating unit 55 to read first one image of eye fundus images recorded on the recording medium and display it on the monitor TV 31.

Figure 8A:
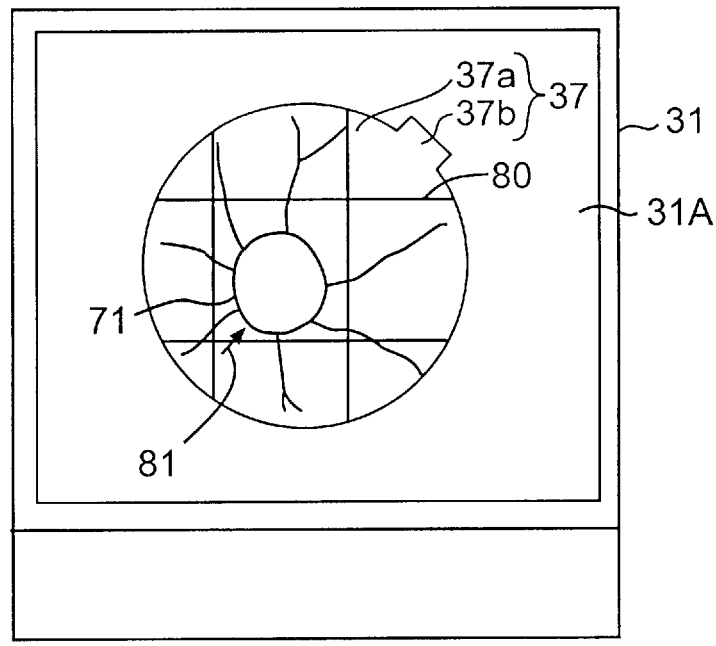
FIG. 8(a) and 8(b) show examples of extraction of an image from the ophthalmological images of FIGS. 7(a) and 7(b).
Figure 8B:
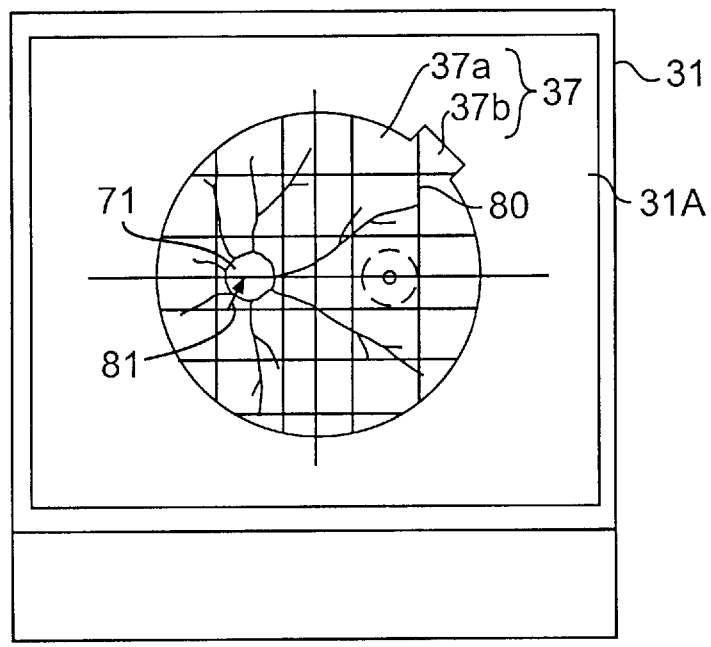

At the same time, divisional lines 80 for extracting desired parts are also superimposed on the eye fundus image 37 as shown in FIG. 8(a) and 8(b). In the mode "retrieval", the arithmetic and control circuit 41 causes the monitor TV 31 to display a mode selection menu representing 1. change of divisional lines 2. extraction of images. By selecting the mode "change of divisional lines" included in the mode "retrieval" by the mouse or keyboard, the divisional lines 80 can be moved with respect to the eye fundus image 37 by a photographing position inputting device 44, such as a mouse or cursor keg of a keyboard. In order to extract, for example, the papilla 71 of the eye fundus image 37, the divisional lines 80 are moved so that the papilla 71 is put in a unit square surrounded by those lines 80. A cursor mark 81 is displayed on the monitor TV 31 as shown in FIG. 8(*a*) and 8(*b*), and then the cursor mark 81 is moved to the unit square by the mouse or cursor key.

Next, the mode "extraction of images" included in the mode "retrieval" is selected by the mouse or cursor key and then the unit square specified by the cursor mark 81 is extracted by the arithmetic and control circuit 41. Image data concerning the papilla 71 extracted from the eye fundus image 37 are temporarily stored in a hard disk or the like of the data recording and regenerating unit 55 by the arithmetic and control circuit 41.

Such extraction of images as mentioned above is applied to the same fundus images in photographing position or photographing angle of view. A part of the eye fundus image to be extracted may be specified by matrices arrayed in rows and columns.

Therefore, if data concerning the photographing position or angle of view as information about photographing conditions obtained when the eye fundus is photographed, are recorded on the recording medium together with data concerning the eye fundus image, a desired part of the eye fundus image can be extracted at any time from the eye fundus images having the same photographing position or angle of view by specifying the part once.

And, one after another, image data concerning many extracted papilla images are temporarily stored in the hard disk by the arithmetic and control circuit 41.

When the mode "display" is selected by the mouse or keyboard, the arithmetic and control circuit 41 causes the image data concerning the papilla 71 stored in the hard disk to be transmitted to the frame memory 45 after a given number of data in order to construct an image for one frame. A resulting papilla image is, one after another, transmitted to the monitor TV to simultaneously display many papilla images *a*1, *a*2, *a*3, and so forth as shown in FIGS. 7(*a*), 7(*b*).

When the mode "transmittance" is selected, a plurality of forwarding addresses are displayed on the monitor TV 31. By selecting one address of them, the image data concerning the papilla 71 stored in the hard disk are transmitted thereto.

Instead of the divisional lines 80, the mouse or cursor key may be used to specify a part to be extracted.

Figure 9:
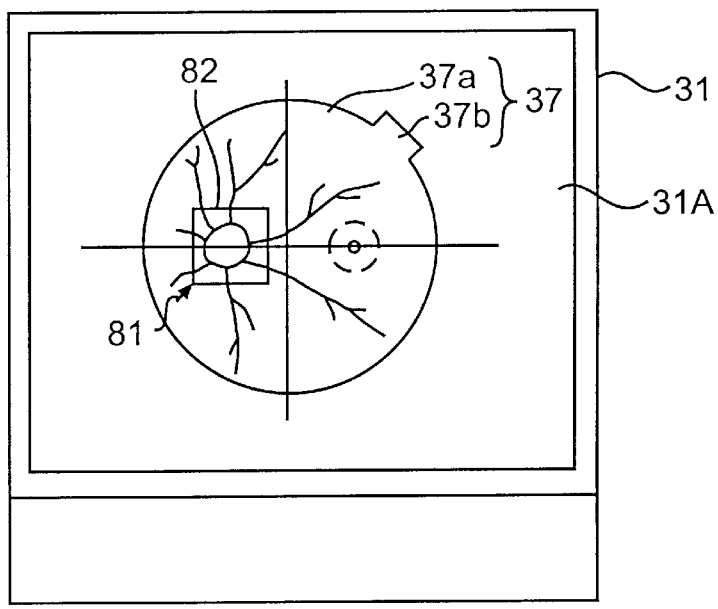
FIG. 9 shows another example of extraction of an image from the ophthalmological images of FIGS. 7(a) and 7(b).

To do so, the arithmetic and control circuit 41 first causes the monitor TV 31 to display a mode selection menu representing 1. specification of a range 2. extraction of images included in the mode "retrieval" and then the mode "specification of a range" is selected by the mouse or keyboard. Thereby, the arithmetic and control circuit 41 causes the monitor TV 31 to display a cursor mark 81 and a square 82 as shown in FIG. 9. This square 82 is free to change its size at an optional position by the mouse or keyboard as the photographing position inputting device 44.

Next, the square 82 is moved by the mouse or cursor key to specify the papilla 71. After that, the mode "extraction of images" is selected, so that the arithmetic and control circuit 41 extracts the papilla 71 of the eye fundus image 37 surrounded by the boundary line 39. Image data concerning the papilla 71 extracted from the eye fundus image 37 are temporarily stored in a hard disk, or the like, of the data recording and regenerating unit 55 by the arithmetic and control circuit 41 in the same way as mentioned above.

Since operations following this are the same as in the case of the divisional lines 80, its description will be omitted.

FIG. 7(*a*) is different in the size of a display square 90 from FIG. 7(*b*). The changing of the size is performed by the photographing position inputting device (photographing range specifying means) 44, such as a mouse, keyboard, or light pen. To perform it, the mode "change of size" is first displayed on the monitor TV 31; and then a desired size is selected by the photographing position inputting device 44. Referring to the display square 90, the size of the display square 90 can be changed without changing a range of the image to be displayed in the square 90, while the range to be displayed can be changed without changing the size of the display square 90. Such extraction as mentioned above is also applied to the yellow spot 72 or the other parts.

<Extraction From Images Different In Photographing Position Or Photographing Angle Of View From Each Other>

Even when a specified part, such as a papilla or yellow spot, is extracted from eye fundus images different in photographing position or photographing angle of view from each other, it may be extracted in the same way as mentioned above, and then respective specified parts may be displayed on the monitor TV 31 as shown in FIG. 7(*a*) and 7(*b*).

In the case of the papilla, if an amount of light of a part to be extracted is less than a given level according to photographing magnification, the arithmetic and control circuit 41 may prohibit the part from being extracted based on its judgment that the part is not the papilla. Likewise, in the yellow spot, if an amount of light of a part to be extracted is more than a given level according to photographing magnification, the arithmetic and control circuit 41 may prohibit the part from being extracted based on its judgment that the part is not the yellow spot.

<Extraction Of The Papilla Based On A Difference In Amount Of Light>

Since the papilla 71 reflects light more than the other parts of the eye fundus, it is possible to extract the papilla from an image of the eye fundus base on a difference in amount of light.

To do so, the mode "retrieval" is first selected and then the arithmetic and control circuit 41 controls the data recording and regenerating unit 55 to cause the frame memory 45 to read an eye fundus image stored in the recording medium. The arithmetic and control circuit 41 detects an amount of light of the eye fundus image formed in the frame memory 45 for each successive address one after another.

Figure 10A:
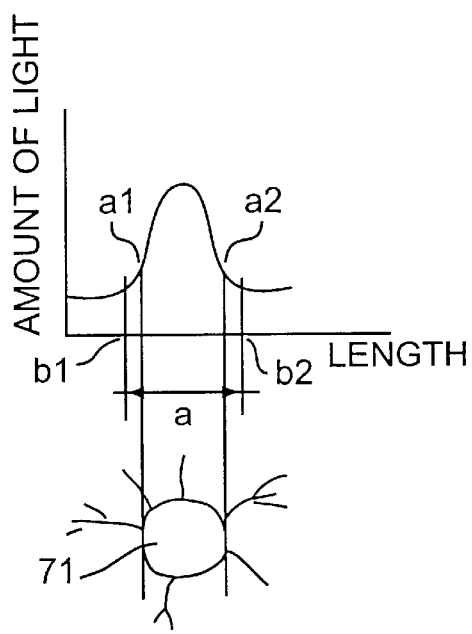
FIG. 10 shows still another example of extraction of an image from the ophthalmological images of FIGS. 7(a) and 7(b).
Figure 10B:
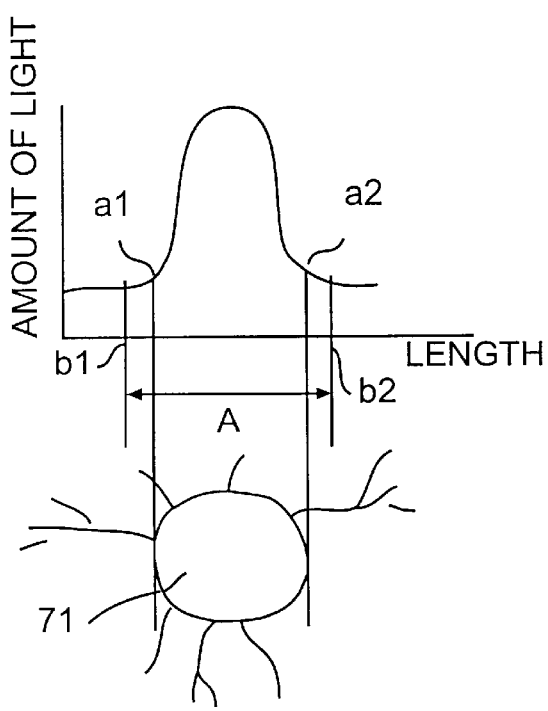
Figure 11A:
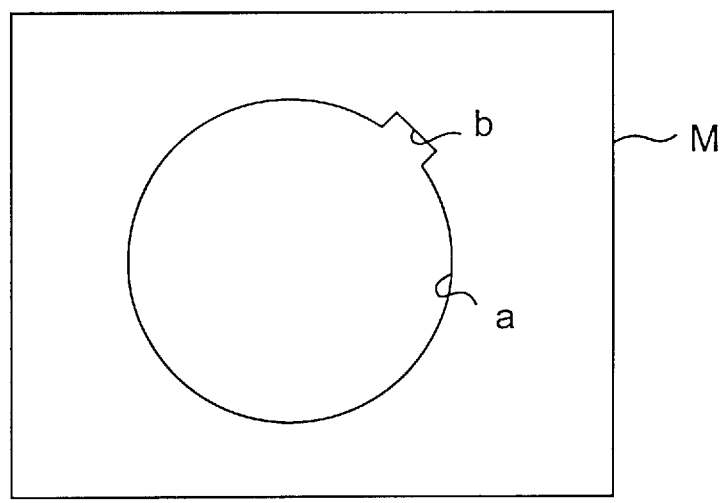
FIG. 11(a) is a view of a conventional mask used for photographing the eye fundus and Fig. 11(b) is a view of an eye fundus image formed on the area CCD by using the mask of FIG. 11(a).
Figure 11B:
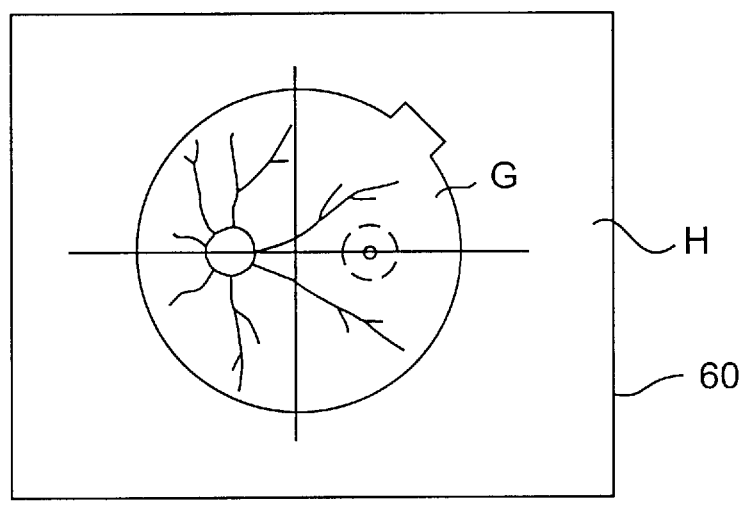

The arithmetic and control circuit 41 calculates a light level variation from a detected amount of light to obtain points *a*1 and *a*2 where a light level (amount of light) abruptly changes and further obtain points *b*1 and *b*2 a given distance away from *a*1 and *a*2 in the low-level direction (see FIG. 10(*a*) and 10(*b*) respectively, according to photographing magnification.

Based on the points *b*1 and *b*2, the arithmetic and control circuit 41 determines the size of a square for extraction and then extracts an image including the papilla 71 and a neighborhood around the papilla 71 from the eye fundus image so as to store data concerning the papilla image in, for example, the hard disk of the data recording and regenerating unit 55 temporarily.

Next, the mode "display" is selected and then the arithmetic and control circuit 41 causes the image data concerning the papilla 71 stored in the hard disk to be transmitted to the frame memory 45 every a given number of data in order to construct an image for one frame. A resulting papilla image is, one after another, transmitted to the monitor TV 31 to simultaneously display many papilla images as shown in FIGS. 7(*a*), 7(*b*).

Only data concerning a picture element having an amount of light more than a given level may be transmitted in order to process the image.

When the mode "transmittance" is selected, a plurality of forwarding addresses are displayed on the monitor TV 31. By selecting one of the addresses, the image data concerning the papilla 71 stored in the hard disk are transmitted.

When the papilla images are simultaneously displayed on the monitor TV 31, an ID number superimposed on each of the papilla images is also displayed. Therefore, in order to make a diagnosis, a detailed eye fundus image including the papilla image provided with the ID number is displayed on the monitor TV by appointing the ID number by means of the mouse or keyboard.

Since the invention is made as mentioned above, only desired data of image data are transmitted; and therefore, the time for transmittance can be shortened.

What is claimed is:

1. An ophthalmological image processing system, comprising:

inputting means for inputting digitized image data corresponding to an image which includes an ophthalmological image;

processing means for processing the image data output by said inputting means;

display means for displaying an image from said processing means;

appointing means for appointing a specific portion within the digitized image data as a range to be extracted;

recording means for recording a plurality of ophthalmological images and photographic-condition information;

a frame memory for storing the plurality of ophthalmological images and for constructing one or more of the plurality of ophthalmological images on said display means; and an arithmetic and control circuit that extracts the specific portion appointed by said appointing means from the digitized image data and causes said recording means to record the specific portion together with the photographic-condition information;

wherein said arithmetic and control circuit selects a plurality of specific portions of the ophthalmological images recorded in said recording means and causes said frame memory to store the images corresponding to one frame and construct them in the form of a matrix and thereafter causes said display means to display the constructed images corresponding to one frame, so that when one of the plurality of images displayed on said display means in the form of a matrix is selected, said arithmetic and control circuit causes said display means to display all of image data of the ophthalmological image which includes selected image data of the selected portions.

2. An ophthalmological image processing system according to claim 1, wherein said appointing means is included in said arithmetic and control circuit that appoints and extracts a portion of an ophthalmological image larger in amount of reflected light than the other portions thereof based on a difference in amount of light between said portion and portions surrounding said portion.

3. An ophthalmological image processing system according to claim 2, wherein said portion larger in amount of reflected light than the other portions of the ophthalmological image is a papilla.

4. An ophthalmological image processing system according to claim 1, wherein said arithmetic and control circuit causes said display means to display divisional lines by which the range to be extracted is specified and which are superimposed upon the ophthalmological image displayed on said display means, and selects one of unit squares defined by the divisional lines displayed on said display means by unit-square selecting means, and thereafter extracts an image within the selected unit square.

5. An ophthalmological image processing system according to claim 1, wherein said arithmetic and control circuit causes said display means to display a frame by which the range to be extracted is specified and which is superimposed upon the ophthalmological image displayed on said display means, and extracts an image within the frame.

6. An ophthalmological image processing system according to claim 5, wherein said frame is freely changeable in dimensions.

* * * * *